United States Patent [19]

Reuter

[11] 4,264,815
[45] Apr. 28, 1981

[54] APPARATUS FOR X-RAY ANALYSIS OF A SPECIMEN WITH LOCAL RESOLUTION

[75] Inventor: Benno Reuter, Lohof, Fed. Rep. of Germany

[73] Assignee: Gesellschaft für Strahlen-und Umweltforschung mbH, Munich, Fed. Rep. of Germany

[21] Appl. No.: 922,726

[22] Filed: Jul. 7, 1978

[30] Foreign Application Priority Data

Jul. 8, 1977 [DE] Fed. Rep. of Germany ....... 2730889

[51] Int. Cl.³ .......................................... G01M 23/00
[52] U.S. Cl. .................................. 250/311; 250/272; 250/321; 250/365; 250/416 TV
[58] Field of Search ............... 250/311, 321, 272, 365, 250/273, 416 TV

[56] References Cited

U.S. PATENT DOCUMENTS

| 1,626,306 | 4/1927 | St. John | 250/272 |
| 3,229,089 | 1/1966 | Sasao | 250/416 TV |
| 3,801,785 | 4/1974 | Barrett | 250/321 |
| 3,961,191 | 6/1976 | Stoner | 250/321 |
| 4,057,745 | 11/1977 | Albert | 250/416 TV |
| 4,099,055 | 7/1978 | Todokoro | 250/311 |

Primary Examiner—Harold A. Dixon
Attorney, Agent, or Firm—Spencer & Kaye

[57] ABSTRACT

In apparatus for examining the material of a specimen with local resolution employing an X-ray probe and operating according to the scanning principle, including a source of X-ray radiation, an optical system for directing X-ray radiation from the source onto the specimen, and a detector disposed for detecting radiation appearing behind the specimen, the source is constituted by a target in which the X-ray radiation is generated, and the optical system acts to focus the X-ray radiation emanating from the target onto the specimen in the form of an X-ray probe.

6 Claims, 2 Drawing Figures

APPARATUS FOR X-RAY ANALYSIS OF A SPECIMEN WITH LOCAL RESOLUTION

BACKGROUND OF THE INVENTION

The present invention relates to an apparatus for the examination of the material of a specimen with local resolution employing an X-ray probe and utilizing the scanning principle, in which apparatus X-ray radiation is generated by a source and is directed onto the specimen by means of an optical system, and the radiation appearing behind the specimen is detected in a detector system.

A device of this type is disclosed in the periodical "Science", Volume 178, pages 608 to 611, November, 1972. In it the synchrotron radiation of an electron synchrotron having an associated optical mirror system and an aperture is utilized for the irradiation while the object is moved physically in a scanning pattern, a loss in intensity of radiation at the optical mirror system and also at the aperture being unavoidable. This is acceptable in practice only if an electron synchrotron or a source with a radiation yield of similar high intensity is available.

A substantial drawback of this device is that its resolving power is limited since, although theoretically the aperture diameter could be limited to 1 micron, this is impossible in practice due to diffraction effects and the fact that, due to roughnesses on the surface of the object, the distance of the aperture from the surface of the object cannot be reduced to an arbitrarily small value.

SUMMARY OF THE INVENTION

It is therefore an object of the present invention to provide a device which permits examination of the material of microscopic specimens with local resolution by means of X-rays, utilizing the scanning principle.

This and other objects are accomplished according to the present invention by generating the X-rays in a target and imaging the X-ray radiation emanating from the target on the specimen by means of an optical system to create the X-ray probe.

According to a particularly advantageous embodiment of the invention, an electron beam is deflected over the target in a scanning pattern in order to produce an X-ray radiation point source which moves in the scanning pattern, and this scanning movement is transmitted by the optical imaging system onto the X-ray probe.

In embodiments of the invention, the electron beam can be generated in a scanning electron microscope, the target is constituted by a thin foil in which the X-rays are generated and their characteristic radiation component e.g. the $K_\alpha$ component, can be displayed in the optical system. The optical system may be a zone plate known from holographic use, as disclosed in the periodical "Scientific Instruments", 1976, Vol. 9, pages 746–751, or an optical mirror system.

According to a particularly favorable embodiment of the invention, the radiation detected by the detector system is used to control the intensity of a cathode ray tube beam which scans the screen of the cathode ray tube of a display device in synchronism with the electron beam of the microprobe.

A particular advantage of the invention is that it permits the entire system to effectively be divided into three parts. The electron optical system, or a laser or proton beam, creates a dot-shaped X-ray source on the target, the imaging system focuses the X-rays from this source on the specimen, and the detector system measures the entire radiation passing through the specimen.

With this assembly of components it is possible to optimally consider the various vacuum requirements and attain high flexibility. For example, a stationary electron probe can also be used. Two-dimensional scanning of the specimen would then, however, have to occur by displacing either the optical system or the specimen in the scanning pattern.

It is thus possible with the present invention, by utilizing the scanning microscope principle, to effect a direct electronic image registration with simultaneous spatial separation of target and specimen, where the specimen is subjected to only a low level of heating and with no energy dispersive intensity measurement, while increasing the theoretical resolving power by reduction of the X-ray source under low vacuum requirements or requirements for a protective gas atmosphere in the specimen chamber and requiring only a small amount of preparatory work on the specimen. Furthermore, it is possible to examine nonconductive specimens.

DESCRIPTION OF THE PREFERRED EMBODIMENTS

Figure 1:
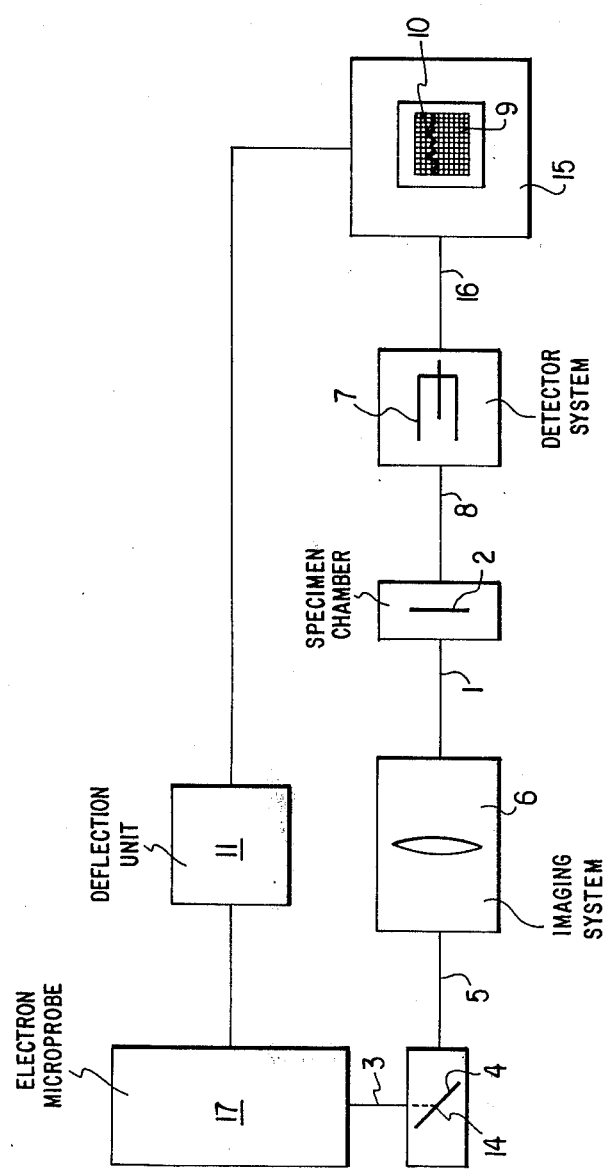
FIG. 1 is a block circuit diagram of the basic construction of apparatus according to the invention.

In the apparatus shown in FIG. 1, the beam 3 of an electron microprobe 17 is focused on a target 4. Under control of a deflection unit 11, the focal spot, or point of convergence, 14 of beam 3 can scan the surface of target 4. In synchronism therewith, an electron beam 10 is deflected over the screen 9 of a CRT display instrument 15.

Figure 2:
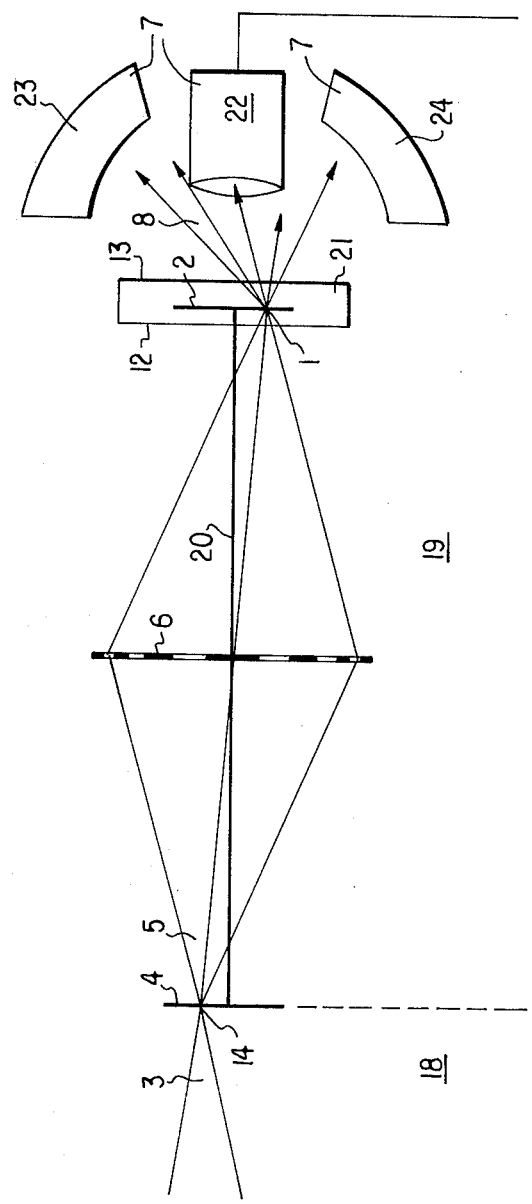
FIG. 2 is a schematic diagram of a radiation generation, imaging and detection arrangement according to the invention.

The characteristic X-ray radiation 5 generated in the target 4 is focused on the specimen by an imaging system 6 and forms the microprobe 1. The entire radiation 8 passing through and beyond the specimen 2, and also any secondary radiation generated in the specimen, is measured with a planar detector system 7. As shown in FIG. 2, system 7 can be composed of a counting tube 22 in the center and two flow counters 23 and 24 on its sides.

The suitably amplified signal 16 from system 7 controls the intensity of the electron beam 10 in the display instrument 15. Since the coordinate of this beam 10 is linearly linked with the position of the X-ray focal spot, i.e. the point of impingement of the microprobe 1, on the surface 2 of the specimen, an X-ray image of the specimen 2 will be obtained on the screen 9. The specimen viewing area, or its magnification, can be set at will by adjusting deflector unit 11. The resolving power, however, is determined by the diameter of the X-ray focal spot on the specimen 2.

The minimum producible electron beam focal spot diameter of the electron beam 3 from the electron microprobe 17 is limited to $1\mu$ due to space charge effects within the beam 3, but the corresponding X-ray focal spot diameter of the microprobe 1 can be optically decreased in size, creating improved resolution. This is possible because of the separate imaging system provided for the X-rays. The required X-ray intensity of the microprobe 1 can be obtained by providing a $10^{-6}$ ampere electron current of the electron beam 3.

FIG. 2 illustrates a second embodiment, and includes a schematic view of the electron beam 3 of a scanning electron microscope with is not shown in detail. The electron beam 3 is focused on the target 4 at one side thereof and creates thereon an X-ray focal spot which can scan the target surface. The target 4 is a foil having a thickness of several microns and made of a material whose K radiation is to be used. For soft X-rays line 113 Å of beryllium, line 44 Å of carbon, line 23.7 Å of iron oxide and line 8.3 Å of aluminum are suitable. The use of a foil as target 4 permits the use of X-ray sources with diameters $<1\mu$. The foil 4 can be mounted to simultaneously serve as a vacuum block, or barrier, between regions 18 and 19.

The imaging system 6 is constituted by a zone plate defining an optical axis 20, and target 4 and specimen 2 extend perpendicular to axis 6. X-rays are emitted from the other side of foil 4 toward plate 6 and about 10% of the X-ray radiation impinging on zone plate 6 is focused on specimen 2 and forms the X-ray probe 1. The specimen 2 is disposed in a chamber 21 which is sealed on both sides by beryllium windows 12 and 13. Thus the gas pressure in the specimen chamber 21 can be set independently of the pressures in the generating chamber 18 and the imaging chamber 19, as well as in the detector chamber. The radiation 8 passing through specimen 2 is recorded by the counting tube 22 disposed in the center. Flow counters 23 and 24 arranged on its sides permit a measurement of the X-ray fluorescence of the specimen 2. Devices 22, 23 and 24 can be constituted by components already well known in the art.

It will be understood that the above description of the present invention is susceptible to various modifications, changes and adaptations, and the same are intended to be comprehended within the meaning and range of equivalents of the appended claims.

What is claimed is:

1. Apparatus for examining a specimen to determine the characteristics of the material of which it is composed, comprising:

means for generating an electron beam;

a target for receiving said electron beam and emitting soft X-ray radiation, said soft X-ray radiation emanating from a point-like source on said target;

a chamber spaced from said target for positioning said specimen;

an optical system interposed between said target and said chamber for focusing the soft X-ray radiation emanating from said target onto said specimen in the form of an X-ray probe;

a detector spaced from said chamber for receiving radiation transmitted therethrough, said detector comprising a centrally located counting tube and at least one flow counter positioned adjacent thereto for measuring the X-ray fluorescence of said specimen;

display means coupled to the output of said detector; and deflection means coupled to said means for generating an electron beam for scanning said electron beam across said target and said X-ray probe across said specimen, said deflection means being further coupled to said display means for synchronization thereof with the scanning of said electron beam across said target.

2. Apparatus as defined in claim 1 wherein said means for generating an electron beam and said deflection means comprise a scanning electron microscope.

3. Apparatus as defined in claim 1 or 2 wherein said target is composed of a foil in which said soft X-ray radiation is produced.

4. Apparatus as defined in claim 3 wherein said foil is selected from the group consisting of beryllium, carbon, iron oxide and aluminum, the characteristic component of said X-ray radiation being the $K_\alpha$ component of said foil materials.

5. Apparatus as defined in claim 1 wherein said display means comprises a cathode ray tube having a screen, said deflection means causing the cathode ray beam of said cathode ray tube to scan said screen in synchronism with the deflection of said electron beam across said target, the intensity of said cathode ray beam being controlled by the output of said detector as a function of the detected radiation.

6. Apparatus as defined in claim 1 wherein said optical system comprises a zone plate.

* * * * *